United States Patent
Nakamura et al.

(10) Patent No.: US 8,026,232 B2
(45) Date of Patent: Sep. 27, 2011

(54) BENZOTHIOPHENE OXIDE DERIVATIVE AND SALT THEREOF

(75) Inventors: Tetsuro Nakamura, Toyama (JP); Hiroshi Kato, Toyama (JP)

(73) Assignee: Toyama Chemical Co., Ltd., Tokyo (JP)

( * ) Notice: Subject to any disclaimer, the term of this patent is extended or adjusted under 35 U.S.C. 154(b) by 0 days.

(21) Appl. No.: 12/994,837

(22) PCT Filed: May 26, 2009

(86) PCT No.: PCT/JP2009/059576
§ 371 (c)(1),
(2), (4) Date: Nov. 26, 2010

(87) PCT Pub. No.: WO2009/145171
PCT Pub. Date: Dec. 3, 2009

(65) Prior Publication Data
US 2011/0077413 A1 Mar. 31, 2011

(30) Foreign Application Priority Data

May 28, 2008 (JP) ................................ 2008-139007

(51) Int. Cl.
*A01N 43/00* (2006.01)
*C07D 205/00* (2006.01)
(52) U.S. Cl. .................................. 514/210.19; 548/950
(58) Field of Classification Search ........................ None
See application file for complete search history.

(56) References Cited

U.S. PATENT DOCUMENTS

| 7,087,594 B2 | 8/2006 | Saitoh et al. |
| 7,468,443 B2 | 12/2008 | Saitoh et al. |
| 2009/0093453 A1 | 4/2009 | Iwakami et al. |
| 2009/0111992 A1 | 4/2009 | Saitoh et al. |
| 2010/0184997 A1 | 7/2010 | Fukushima et al. |

FOREIGN PATENT DOCUMENTS

| WO | 03 035647 | 5/2003 |
| WO | 2007 125913 | 11/2007 |
| WO | 2008 016107 | 2/2008 |

OTHER PUBLICATIONS

International Search Report issued Jun. 23, 2009 in PCT/JP09/59576 filed May 26, 2009.
Wermuth, C.G., Translated under the supervision of Hiroshi NAGASE, Saishin Soyaku Kagaku Last volume, Technomics, Inc., pp. 307-310, III. Kangenteki na Seitainai Kasseika, (Sep. 25, 1999).

*Primary Examiner* — Sun Jae Loewe
(74) *Attorney, Agent, or Firm* — Oblon, Spivak, McClelland, Maier & Neustadt, L.L.P.

(57) ABSTRACT

Disclosed is a benzothiophene oxide derivative represented by the general formula (wherein $R^1$ and $R^2$ are the same or different and each represents one or more groups selected from a hydrogen atom, a halogen atom, an alkyl group, an aryl group, an aralkyl group, an alkoxy group, an aryloxy group, an alkenyl group, an amino group, a heterocyclic group, an amino group, a hydroxyl group, a carboxyl group, an oxo group and the like; $R^3$ represents an alkylamino group, an amino group, a hydroxyl group or the like; and m and n are the same or different and each represents an integer of 1-6) or a salt thereof, which is useful as a prodrug of a benzothiophene derivative or a salt thereof.

12 Claims, 1 Drawing Sheet

BENZOTHIOPHENE OXIDE DERIVATIVE AND SALT THEREOF

CROSS-REFERENCE TO RELATED APPLICATIONS

This application is a 371 of PCT/JP09/59576 filed May 26, 2009 and claims the benefit of JP 2008-139007 filed May 28, 2008.

TECHNICAL FIELD

The present invention relates to a benzothiophene oxide derivative or a salt thereof which is useful as a prodrug of a therapeutic agent for central and peripheral nerve diseases.

BACKGROUND ART

In the study of a therapeutic agent, many drugs have been found by a method using an in vitro model. However, some drugs have a low bioavailability and have limited therapeutic usefulness. In order to avoid these problems, there have been known means of chemically modifying a compound to form a prodrug.

A benzothiophene derivative, which is typified by 1-(3-(2-(1-benzothiophen-5-yl)ethoxy)propyl)-3-azetidinol, has a neuroprotective activity, a nerve regeneration promoting activity and a neurite outgrowth promoting activity and is a useful compound as a therapeutic agent for central and peripheral nerve diseases (Patent Document 1). However, the benzothiophene oxide derivative described in the present application has never been known before.

PRIOR ARTS REFERENCE

Patent Document

PATENT DOCUMENT 1: International Publication No. WO 03/035647 pamphlet

SUMMARY OF INVENTION

Problems to be Solved by the Invention

A compound which has a neuroprotective activity, a nerve regeneration promoting activity and a neurite outgrowth promoting activity and is useful as a therapeutic agent for central and nerve diseases has been strongly desired.

Means for Solving the Problems

Under these circumstances, the present inventors have found that a benzothiophene oxide derivative represented by the following general formula [1] or a salt thereof is converted into a benzothiophene derivative represented by the following general formula [2] or a salt thereof in the living body and is useful as a prodrug of a corresponding benzothiophene derivative or a salt thereof:

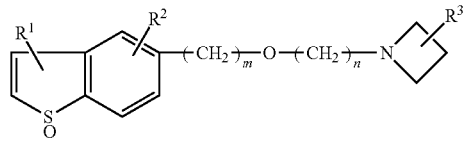

[Formula 1]

wherein, $R^1$ and $R^2$ are the same or different and represent one or more groups selected from a hydrogen atom, a halogen atom, an alkyl, aryl, aralkyl, alkoxy, aryloxy, alkylthio, arylthio, alkenyl, alkenyloxy, amino, alkylsulfonyl, arylsulfonyl, carbamoyl or heterocyclic group which may be substituted, an amino, hydroxyl or carboxyl group which may be protected, a nitro group and an oxo group; $R^3$ represents an alkylamino group which may be substituted, an amino or hydroxyl group which may be protected; and m and n are the same or different and each represent an integer of 1 to 6;

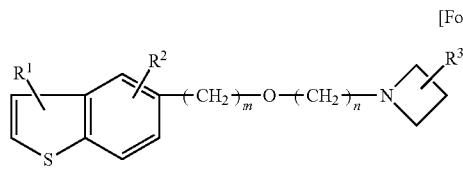

[Formula 2]

wherein, $R^1$, $R^2$, $R^3$, m and n have the same meaning as described above.

Further, the present inventors have found that by administering a benzothiophene oxide derivative or a salt thereof, the concentration of a corresponding benzothiophene derivative or a salt thereof in the blood is not rapidly increased and is maintained at a high concentration over a long period of time and have completed the present invention.

Advantages of the Invention

A benzothiophene oxide derivative represented by the general formula [1] or a salt thereof is useful as a prodrug of a corresponding benzothiophene derivative or a salt thereof. Further, a benzothiophene oxide derivative represented by the general formula [1] or a salt thereof is useful as a drug substance of a long-acting preparation of a corresponding benzothiophene derivative or a salt thereof.

DESCRIPTION OF EMBODIMENTS

Figure 1:
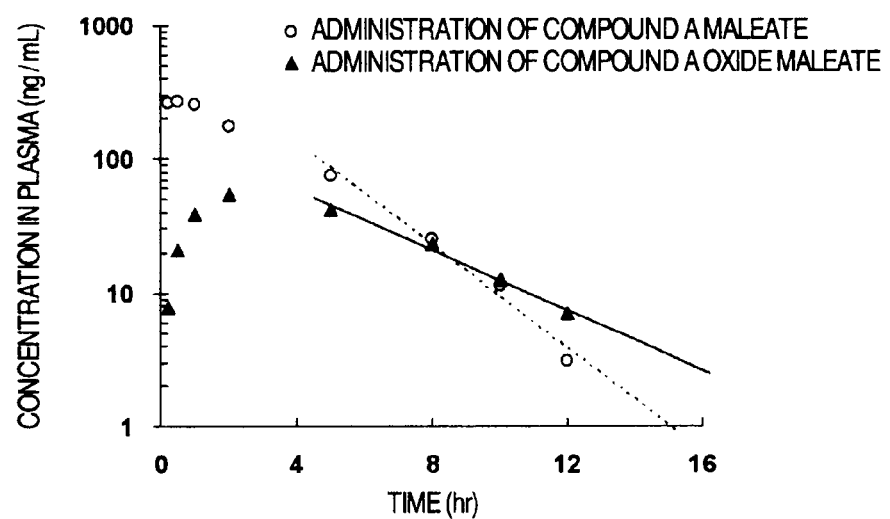
FIG. 1 is a graph showing the concentration of a compound A in the plasma after administering a compound A maleate and a compound A oxide maleate.

The present invention will be described in detail below.

In this description, unless otherwise specified, each term has the following meaning.

The term "a compound A" means "1-(3-(2-(1-benzothiophen-5-yl)ethoxy)propyl)azetidin-3-ol".

The term "a compound A oxide" means "1-(3-(2-(1-benzothiophen-5-yl)ethoxy)propyl)azetidin-3-ol S-oxide".

The term "a halogen atom" means a fluorine atom, a chlorine atom, a bromine atom or an iodine atom; the term "an alkyl group" means a linear or branched $C_{1-12}$ alkyl group such as methyl, ethyl, propyl, isopropyl, butyl, isobutyl, tert-butyl, pentyl, hexyl, heptyl and octyl; the term "a lower alkyl group" means a linear or branched $C_{1-6}$ alkyl group such as methyl, ethyl, propyl, isopropyl, butyl, isobutyl, tert-butyl, pentyl and hexyl; the term "an alkenyl group" means a $C_{2-12}$ alkenyl group such as vinyl, propenyl, butenyl, pentenyl, hexenyl, heptenyl and octenyl; the term "a lower alkenyl group" means a $C_{2-6}$ alkenyl group such as vinyl, propenyl, butenyl, pentenyl and hexenyl; the term "an acylalkyl group" means, for example, a group such as acetylmethyl, benzoylmethyl, p-nitrobenzoylmethyl, p-bromobenzoylmethyl, p-methoxybenzoylmethyl and 1-benzoylethyl; the term "an acyloxyalkyl group" means, for example, a group such as acetoxymethyl, propionyloxymethyl and pivaloyloxymethyl, the term "an arylthioalkyl group" means, for example, a group such as phenylsulfenylmethyl and 2-(p-nitrophenylsulfenyl)ethyl; the term "an arylsulfonylalkyl group" means, for example, a group such as p-toluenesulfonylethyl; the term "a nitrogen-containing heterocyclic alkyl group" means, for example, a group such as phthalimidomethyl and succinimidomethyl; the term "a cycloalkyl group" means, for example, a $C_{3-8}$ cycloalkyl group such as cyclopropyl, cyclobutyl, cyclopentyl and cyclohexyl, the term "an alkylthioalkyl group" means, for example, a $C_{1-6}$ alkylthio $C_{1-6}$ alkyl group such as methylthiomethyl, ethylthiomethyl and propylthiomethyl, the term "an alkoxyalkyl group" means, for example, a $C_{1-6}$ alkyloxy $C_{1-6}$ alkyl group such as methoxymethyl and 1-ethoxyethyl; and the term "an aralkyloxyalkyl group" means, for example, an ar-$C_{1-6}$ alkyloxy $C_{1-6}$ alkyl group such as benzyloxymethyl and phenethyloxymethyl.

The term "alkoxy group" means a linear or branched $C_{1-12}$ alkyloxy group such as methoxy, ethoxy, propoxy, isopropoxy, butoxy, isobutoxy, tert-butoxy, pentyloxy, hexyloxy, heptyloxy and octyloxy; the term "lower alkoxy group" means a linear or branched $C_{1-6}$ alkyloxy group such as methoxy, ethoxy, propoxy, isopropoxy, butoxy, isobutoxy, tert-butoxy, pentyloxy and hexyloxy; and the term "alkenyloxy group" means a $C_{2-12}$ alkenyloxy group such as vinyloxy, propenyloxy, butenyloxy, pentenyloxy, hexenyloxy, heptenyloxy and octenyloxy.

The term "alkylthio group" means a $C_{1-12}$ alkylthio group such as methylthio, ethylthio, propylthio, isopropylthio, butylthio, isobutylthio, tert-butylthio, pentylthio, hexylthio, heptylthio and octylthio; and the term "lower alkylthio group" means a $C_{1-6}$ alkylthio group such as methylthio, ethylthio, propylthio, isopropylthio, butylthio, isobutylthio, tert-butylthio, pentylthio and hexylthio.

The term "aryl group" means a phenyl group, a naphthyl group, an indanyl group and an indenyl group; the term "aryloxy group" means a phenyloxy group, a naphthyloxy group, an indanyloxy group and an indenyloxy group; the term "aralkyl group" means an ar-$C_{1-6}$ alkyl group such as benzyl, diphenylmethyl, trityl and phenethyl; and the term "arylthio group" means a phenylthio group, a naphthylthio group, an indanylthio group and an indenylthio group.

The term "acyl group" means a $C_{2-12}$ alkanoyl group such as a formyl group, acetyl, isovaleryl, propionyl and pivaloyl, an aralkylcarbonyl group such as benzylcarbonyl and an aroyl group such as benzoyl and naphthoyl; the term "alkyloxycarbonyl group" means, for example, a linear or branched $C_{1-12}$ alkyloxycarbonyl group such as methoxycarbonyl, ethoxycarbonyl, 1,1-dimethylpropoxycarbonyl, isopropoxycarbonyl, 2-ethylhexyloxycarbonyl, tert-butoxycarbonyl and tert-pentyloxycarbonyl; the term "aralkyloxycarbonyl group" means, for example, an ar-$C_{1-6}$ alkyloxycarbonyl group such as a benzyloxycarbonyl group and a phenethyloxycarbonyl group; the term "aryloxycarbonyl group" means, for example, a group such as phenyloxycarbonyl, and the term "heterocyclic oxycarbonyl group" means, for example, a group such as 2-furfuryloxycarbonyl and 8-quinolyloxycarbonyl.

The term "alkylsulfonyl group" means a $C_{1-12}$ alkylsulfonyl group such as methylsulfonyl, ethylsulfonyl, propylsulfonyl, isopropylsulfonyl, butylsulfonyl, isobutylsulfonyl, sec-butylsulfonyl, tert-butylsulfonyl, pentylsulfonyl, hexylsulfonyl, heptylsulfonyl and octylsulfonyl; the term "lower alkylsulfonyl group" means, for example, a $C_{1-6}$ alkylsulfonyl group such as methylsulfonyl, ethylsulfonyl and propylsulfonyl; and the term "arylsulfonyl group" means a group such as phenylsulfonyl, p-toluenesulfonyl and naphthylsulfonyl.

The term "alkylamino group" means a mono- or di-$C_{1-6}$ alkylamino group such as methylamino, ethylamino, propylamino, isopropylamino, butylamino, dimethylamino, diethylamino, diisopropylamino and dibutylamino.

The term "heterocyclic group" means a heterocyclic group of a 5- or 6-membered ring, condensed ring, or crosslinked ring containing at least one or more heteroatoms selected from a nitrogen atom, an oxygen atom or a sulfur atom such as pyrrolidinyl, piperidinyl, piperazinyl, homopiperazinyl, homopiperidinyl, morpholyl, thiomorpholyl, tetrahydroquinolinyl, tetrahydroisoquinolyl, quinuclidinyl, imidazolinyl, pyrrolyl, imidazolyl, pyrazolyl, pyridyl, pyrimidyl, quinolyl, quinolizinyl, thiazolyl, tetrazolyl, thiadiazolyl, pyrrolinyl, pyrazolinyl, pyrazolidinyl, purinyl, furyl, thienyl, benzothienyl, pyranyl, isobenzofuranyl, oxazolyl, isoxazolyl, benzofuranyl, indolyl, benzimidazolyl, benzoxazolyl, benzisoxazolyl, benzothiazolyl, quinoxalyl, dihydroquinoxalyl, 2,3-dihydrobenzothienyl, 2,3-dihydrobenzopyrrolyl, 2, 3-4H-1-thianaphthyl, 2,3-dihydrobenzofuranyl, benzo[b]dioxanyl, imidazo[2,3-a]pyridyl, benzo[b]piperazinyl, chromenyl, isothiazolyl, isoxazolyl, oxadiazolyl, pyridazinyl, isoindolyl, isoquinolyl, 1,3-benzodioxonyl and 1,4-benzodioxanyl.

The term "oxygen-containing heterocyclic group" means, for example, a group such as 2-tetrahydropyranyl and 2-tetrahydrofuranyl; the term "sulfur-containing heterocyclic group" means, for example, a group such as tetrahydrothiopyranyl, the term "substituted silyl group" means, for example, a group such as trimethylsilyl, triethylsilyl and tributylsilyl, and the term "alkylsilylalkyl group" means, for example, a group such as 2-(trimethylsilyl)ethyl.

Amino protecting groups include all groups which are usable as a usual amino protecting group, and the examples include the groups described in "Protective Groups in Organic Synthesis" by W. Greene et al., pp. 494-615, 3rd edition, 1999, John Wiley & Sons, INC. Specific examples include an acyl group, an alkyloxycarbonyl group, an aralkyloxycarbonyl group, an aryloxycarbonyl group, an aralkyl group, an alkoxyalkyl group, an aralkyloxyalkyl group, an arylthio group, an alkylsulfonyl group, an arylsulfonyl group and a substituted silyl group.

Hydroxyl protecting groups include all groups which are usable as a usual hydroxyl protecting group, and the examples include the groups described in "Protective Groups in Organic Synthesis" by W. Greene et al., pp. 17-245, 3rd edition, 1999, John Wiley & Sons, INC. Specific examples include an acyl group, an alkyloxycarbonyl group, an aralkyloxycarbonyl group, a heterocyclic oxy carbonyl group, an alkyl group, an alkenyl group, an aralkyl group, an oxygen-containing heterocyclic group, a sulfur-containing heterocyclic group, an alkoxyalkyl group, an aralkyloxyalkyl group, an alkylsulfonyl group, an arylsulfonyl group and a substituted silyl group.

Carboxyl protecting groups include all groups which are usable as a usual carboxyl protecting group, and examples include groups described in "Protective Groups in Organic Synthesis" by W. Greene et al., pp. 369-453, 3rd edition, 1999, John Wiley & Sons, INC. Specific examples include an alkyl group, an alkenyl group, an aryl group, an aralkyl group, an acylalkyl group, an arylthioalkyl group, an arylsulfonylalkyl group, an oxygen-containing heterocyclic group, an alkylsilylalkyl group, an acyloxyalkyl group, a nitrogen-containing heterocyclic alkyl group, a cycloalkyl group, an alkoxyalkyl group, an aralkyloxyalkyl group, an alkylthioalkyl group and a substituted silyl group.

Examples of a substituent for the alkyl group, the aryl group, the aralkyl group, the alkoxy group, the aryloxy group, the alkylthio group, the arylthio group, the alkenyl group, the alkenyloxy group, the amino group, the alkylsulfonyl group, the arylsulfonyl group, the carbamoyl group and the heterocyclic group in $R^1$ and $R^2$ and a substituent for the alkylamino group in $R^3$ include a group selected from a halogen atom, a lower alkyl group, a cycloalkyl group, an aryl group, a lower alkoxy group, an aryloxy group, a lower alkylthio group, an arylthio group, a lower alkenyl group, a lower alkylsulfonyl group, an arylsulfonyl group, an alkylamino group, an amino group which may be protected, a hydroxyl group which may be protected, a carboxyl group which may be protected, an acyl group and a heterocyclic group.

Examples of a salt of a compound represented by the general formula [1] can include a salt at a generally known basic group such as an amino group, or a salt at an acidic group such as a hydroxyl or carboxyl group.

Examples of the salt at a basic group include a salt with a mineral acid such as hydrochloric acid, hydrobromic acid, nitric acid and sulfuric acid; a salt with an organic carboxylic acid such as formic acid, acetic acid, citric acid, oxalic acid, fumaric acid, maleic acid, succinic acid, malic acid, tartaric acid, aspartic acid, trichloroacetic acid and trifluoroacetic acid; and a salt with a sulfonic acid such as methanesulfonic acid, benzenesulfonic acid, p-toluenesulfonic acid, mesitylenesulfonic acid and naphthalenesulfonic acid.

Examples of the salt at an acidic group include a salt with an alkali metal such as sodium and potassium; salts with an alkaline-earth metal such as calcium and magnesium; an ammonium salt; and a salt with a nitrogen-containing organic base such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine and N,N-dibenzylethylenediamine.

Among the above-mentioned salts, a preferred salt includes a pharmacologically acceptable salt.

When an isomer (for example, an optical isomer, a geometric isomer and a tautomer) is present in the benzothiophene oxide derivative represented by the general formula [1] or a salt thereof, the present invention includes all those isomers and includes a hydrate, a solvate and all crystal forms.

Preferred examples of the benzothiophene oxide derivative represented by the general formula [1] and the salt thereof include the following compounds.

Preferred is a compound in which $R^1$ is a hydrogen atom.

Preferred is a compound in which $R^2$ is a hydrogen atom, a halogen atom, or an alkoxy group and more preferred is a compound in which $R^2$ is a hydrogen atom.

Preferred is a compound in which $R^3$ is a hydroxyl group.

Preferred is a compound in which m is 2.

Preferred is a compound in which n is 2 or 3 and more preferred is a compound in which n is 3.

Further, most preferred is a compound in which $R^1$ and $R^2$ are a hydrogen atom, $R^3$ is a hydroxyl group, m is 2 and n is 3.

Next, a method of producing a benzothiophene oxide derivative of the present invention will be described. A benzothiophene oxide derivative represented by the general formula [1] can be produced, for example, by the following production method.

A benzothiophene oxide derivative represented by the general formula [1] can be produced by the oxidation of a benzothiophene derivative represented by the general formula [2].

A benzothiophene derivative represented by the general formula [2] can be produced, for example, by the production method described in Patent Document 1.

The solvent used in the reaction is not particularly limited as long as it does not adversely affect the reaction, but examples of the solvent include water; halogenated hydrocarbons such as methylene chloride, chloroform and dichloroethane; aliphatic hydrocarbons such as hexane and cyclohexane; and pyridine, which may be used by mixing two or more kinds.

Examples of the oxidizing agent used in the reaction include hydrogen peroxide; peroxides such as peracetic acid, perbenzoic acid and m-chloroperbenzoic acid; peroxides such as tert-butyl peroxide; and sodium metaperiodate. The amount used of the oxidizing agent is 1 to 50 times by mole and preferably 1 to 10 times by mole with respect to the benzothiophene derivative.

The reaction may be carried out usually at −50 to 100° C. and preferably at −20 to 20° C. for 30 minutes to 48 hours.

A benzothiophene oxide derivative represented by the general formula [1] or a salt thereof is converted into a corresponding benzothiophene derivative or a salt thereof in the living body and is therefore useful as a prodrug of the benzothiophene derivative or a salt thereof. Further, since the concentration of the benzothiophene derivative or a salt thereof in the blood is not rapidly increased and is maintained at a high concentration over a long period of time by administering a benzothiophene oxide derivative of the present invention represented by the general formula [1] or a salt thereof, the benzothiophene oxide derivative or a salt thereof is useful as a drug substance of a long-acting preparation of a corresponding benzothiophene derivative or a salt thereof.

A benzothiophene oxide derivative represented by the general formula [1] or a salt thereof can be formulated into pharmaceutical preparations such as oral agents (such as a tablet, a capsule, a powder, a granule, a fine powder, a pill, a suspension, an emulsion, a solution and a syrup) and injections, by incorporating various types of pharmaceutical additives such as an excipient, a binder, a disintegrant, a disintegration inhibitor, an anticaking/antiadhesion agent, a lubricant, an absorption/adsorption carrier, a solvent, an extender, a tonicity agent, a solubilizing agent, an emulsifying agent, a suspending agent, a thickening agent, a coating agent, an absorption promoter, a gelation/coagulation promoter, a light stabilizer, a preservative, a desiccating agent, an emulsion/suspension/dispersion stabilizer, a coloration preventing agent, a deoxidizer/antioxidant, a corrigent agent, a coloring agent, a foaming agent, an antifoaming agent, a soothing agent, an antistatic agent and a buffering/pH adjusting agent.

The above-mentioned preparations are formulated in the usual manner.

Oral solid preparations such as a tablet, a powder, or a granule may be prepared in the usual manner using pharmaceutical additives for solid formulations, including: an excipient such as lactose, sucrose, sodium chloride, glucose, starch, calcium carbonate, kaolin, crystalline cellulose, anhydrous dibasic calcium phosphate, partly pregelatinized starch, corn starch and alginic acid; a binder such as a simple syrup, a glucose solution, a starch solution, a gelatin solution, polyvinyl alcohol, polyvinyl ether, polyvinylpyrrolidone, carboxymethylcellulose, shellac, methylcellulose, ethylcellulose, sodium alginate, gum arabic, hydroxypropylmethylcellulose, hydroxypropylcellulose, water and ethanol; a disintegrant such as dry starch, alginic acid, agar powders, starch, crosslinked polyvinylpyrrolidone, crosslinked carboxymethylcellulose sodium, carboxymethylcellulose calcium and sodium starch glycolate; a disintegration inhibitor such as stearyl alcohol, stearic acid, cacao butter and hydrogenated oil; an anticaking/antiadhesion agent such as aluminum silicate, calcium hydrogen phosphate, magnesium oxide, talc and anhydrous silicic acid; a lubricant such as carnauba wax, light anhydrous silicic acid, aluminum silicate, magnesium silicate, hydrogenated oil, hydrogenated vegetable oil derivatives, sesame oil, bleached beeswax, titanium oxide, a dry aluminum hydroxide gel, stearic acid, calcium stearate, magnesium stearate, talc, calcium hydrogen phosphate, sodium lauryl sulfate and polyethylene glycol; an absorption promoter such as a quaternary ammonium salt, sodium lauryl sulfate, urea and an enzyme, and an absorption/adsorption carrier such as starch, lactose, kaolin, bentonite, anhydrous silicic acid, hydrous silicon dioxide, magnesium aluminometasilicate and colloidal silicic acid.

A tablet may be processed into a tablet coated with a common coating agent, for example, a sugar-coated tablet, a gelatin-coated tablet, a gastric coated tablet, an enteric coated tablet and a water-soluble film coated tablet, where necessary.

A capsule is prepared by mixing with the various types of medicinal products exemplified above and filling the resulting mixture in a hard gelatin capsule and soft capsule.

These oral solid preparations may also be formulated into an aqueous or oily suspension, a solution, a syrup and an elixir by a common method using the above-mentioned various types of additives for liquid formulations such as a solvent, an extender, a tonicity agent, a solubilizing agent, an emulsifier, a suspending agent or a thickening agent.

An injection may be prepared by a common method using pharmaceutical additives for liquid formulations, including: a diluent such as water, ethyl alcohol, macrogol, propylene glycol, citric acid, acetic acid, phosphoric acid, lactic acid, sodium lactate, sulfuric acid and sodium hydroxide; a pH adjusting agent and a buffering agent such as sodium citrate, sodium acetate and sodium phosphate; a stabilizer such as sodium pyrosulfite, ethylenediaminetetraacetic acid, thioglycolic acid and thiolactic acid; a tonicity agent such as sodium chloride, glucose, mannitol or glycerin; a solubilizing agent such as carboxymethylcellulose sodium, propylene glycol, sodium benzoate, benzyl benzoate, urethane, ethanolamine and glycerin; a soothing agent such as calcium gluconate, chlorobutanol, glucose and benzyl alcohol; and a local anesthetic.

A method of administering the above-mentioned preparations is not particularly limited, but is arbitrarily determined depending on the form of a preparation, the age or sex of a patient, other conditions and the degree of the symptoms of a patient.

The dosage of the active ingredient of the preparation of the present invention is arbitrarily selected depending on the usage, the age or sex of a patient, the form of disease, and other conditions. However, in general, the preparation of the present invention may be administered at a dosage of 0.1 to 1000 mg for an adult once or several times per day.

EXAMPLES

Subsequently, the present invention will be described by Examples and Test Examples, but the present invention is not limited thereto.

Abbreviation in Examples has the following meaning:
DMSO-$d_6$: Deuterated Dimethyl Sulfoxide Example 1

Production of Compound A Oxide Maleate

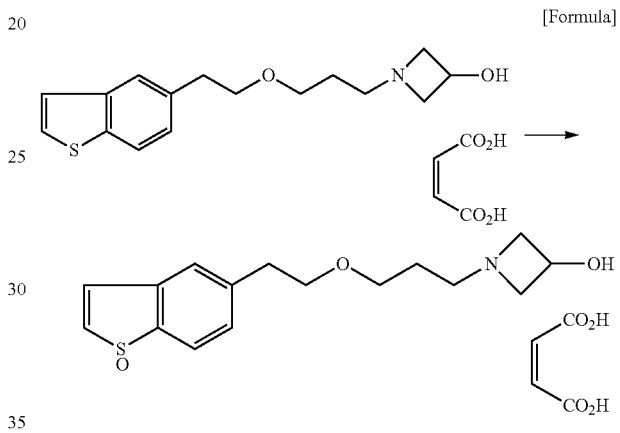

[Formula]

A mixture was prepared by adding 5 mol/L of an aqueous sodium hydroxide solution to a mixed solution of 7.00 g of 1-(3-(2-(1-benzothiophen-5-yl)ethoxy)propyl)azetidin-3-ol maleate, 35 mL of water and 35 mL of ethyl acetate under cooling with ice and the pH of the resulting mixture was adjusted to 11.7. An organic layer was fractionated and sequentially washed with water and saturated saline. Thereafter, the organic layer was dried with anhydrous magnesium sulfate and the solvent was distilled off under reduced pressure. To the resulting residue was added 25 mL of methylene chloride and 6.62 mL of trifluoroacetic acid was dropwise added at 6 to 7° C. Subsequently, to the resulting mixture was dividedly added 3.65 g of m-chloroperbenzoic acid at 4 to 7° C., following by stirring at the same temperature for two hours. An insoluble matter was filtered off and the residue was washed with water. The filtrate and washing water were combined and an aqueous layer was fractionated. The organic layer was extracted with water, and the combined aqueous layer was washed with ethyl acetate, followed by adding ethyl acetate to adjust the pH to 10.5 with potassium carbonate. The aqueous layer was fractionated and extracted with chloroform, and then the extract was dried with anhydrous magnesium sulfate, followed by concentrating to 16.1 g under reduced pressure.

To the resulting solution was dropwise added 4.5 mL of a methanol solution of 1.20 g of maleic acid under cooling with ice, and then 13.5 mL of ethyl acetate was dropwise added, followed by stirring at the same temperature for one hour. A solid matter was filtered off to obtain 3.36 g of 1-(3-(2-(1-benzothiophen-5-yl)ethoxy)propyl)azetidin-3-ol S-oxide maleate.

$^1$H-NMR (DMSO-d$_6$) δ value: 1.74-1.63 (m, 2H), 2.91 (t, 2H, J=6.5 Hz), 3.11 (t, 2H, J=7.6 Hz), 3.42 (t, 2H, J=5.9 Hz), 3.63 (t, 2H, J=6.5 Hz), 3.82-3.73 (m, 2H), 4.28-4.15 (m, 2H), 4.51-4.41 (m, 1H), 6.03 (s, 2H), 6.14-6.09 (m, 1H), 7.43-7.38 (m, 1H), 7.43 (d, 1H, J=6.1 Hz), 7.46 (d, 1H, J=6.1 Hz), 7.57-7.53 (m, 1H), 7.90 (d, 1H, J=7.6 Hz)

Test Example 1

In the compound A administration solution, the concentration of the compound A maleate was adjusted to be 14 mg/mL by dissolving the compound A maleate in a physiological saline solution. In the compound A oxide administration solution, the concentration of the compound A oxide maleate was adjusted to be 14.54 mg/mL by dissolving the compound A oxide maleate in a physiological saline solution.

Each of the administration solutions was orally administered to rats (Crl: CD strain male rat: 8 weeks old) without fasting. The dosage was set at 56 mg/kg for the compound A administration group and 58 mg/kg for the compound A oxide administration group.

At 0.25, 0.5, 1, 2, 5, 8, 10 and 12 hours after the administration, for each group, heparinized whole blood was collected from the aorta abdominalis under mild ether anesthesia, and then the rats were killed by exsanguination and the brains were excised.

The collected blood was centrifuged at 4° C. for 10 minutes at approximately 1600×g to obtain the plasma. To 100 μL of the resulting plasma was added 900 μL of distilled water containing 25 ng/mL of the internal standard substance and 25 μL of phosphoric acid, and the resulting mixture was stirred, followed by adding to a solid-phase extraction plate (Oasis HLB 10 mg or 30 mg, manufactured by Waters) which was conditioned with methanol and distilled water. The solid-phase extraction plate was washed with 2 mL of distilled water, followed by eluting with 2 mL of acetonitrile. The eluate was concentrated and dried-up and then dissolved in a mobile phase A solution, followed by centrifuging at 4° C. for 10 minutes at approximately 1600×g. The resulting supernatant was subjected to a liquid chromatography-tandem mass spectrometer to determine the concentration of the compound A in the plasma of each group.

The excised brains were homogenized with 25% ammonia water/methanol (1:49) (10-fold volume of the wet brain weight) and then 2 mL of the homogenate was centrifuged at 4° C. for 10 minutes at approximately 1600×g to separate the supernatant. To the sediment was added 2 mL of 25% ammonia water/methanol (1:49), followed by centrifuging at 4° C. for 10 minutes at approximately 1600×g. These supernatants were combined and concentrated and dried-up and then dissolved in 1 mL of distilled water containing 25 ng/mL of the internal standard substance. To the resulting solution was added 25 μL of phosphoric acid and the resulting mixture was stirred, followed by subjecting to a solid-phase extraction operation similar to that for the above plasma. The resulting eluate was concentrated and dried-up and then dissolved in the mobile phase A solution or 50% methanol, followed by centrifuging at 4° C. for 10 minutes at approximately 1600×g. The resulting supernatant was subjected to the liquid chromatography-tandem mass spectrometer to determine the concentration of the compound A in the brain of each group.

Figure 2:
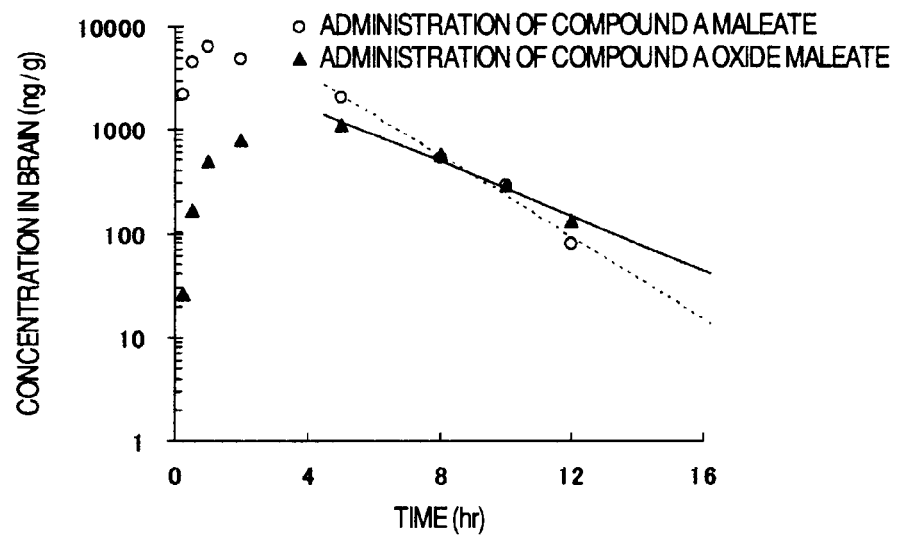
FIG. 2 is a graph showing the concentration of a compound A in the brain after administering a compound A maleate and a compound A oxide maleate.

The results are shown in FIGS. 1 and 2.

Table 1 shows the elimination half-life ($T_{1/2}$) and mean residence time (MRT) of the compound A after the administration of the compound A maleate and the compound A oxide maleate.

The following instruments and conditions were used for the measurement of the concentration of the compound A.

Liquid chromatography-tandem mass spectrometer

Liquid chromatography equipment: ACQUITY HPLC System (Waters)

Mass spectrometer: API 5000 (Applied Biosystems/MDS SCIEX)

Column: ACQUITY HPLC BEH C18 1.7 μm, Inside diameter 2.1 mm×Length 100 mm (Waters)

Column temperature: 40° C.

Mobile Phase

Mobile phase A solution: Acetonitrile/0.2 mol/L formic acid buffer (pH: 5.5)/distilled water (10:5:85 (v/v/v))

Mobile phase B solution: Acetonitrile/0.2 mol/L formic acid buffer (pH: 5.5)/distilled water (90:5:5 (v/v/v))

Step-Gradient Conditions 0 to 3 min: 95% of the mobile phase A solution, 5% of the mobile phase B solution 3 to 6 min: 90% of the mobile phase A solution, 10% of the mobile phase B solution 6 to 9 min: 85% of the mobile phase A solution, 15% of the mobile phase B solution 9 to 10 min: 80% of the mobile phase A solution, 20% of the mobile phase B solution 10 to 11 min: 25% of the mobile phase A solution, 75% of the mobile phase B solution Flow rate: 0.4 mL/min Internal standard substance: 2-[2-(diethylamino)ethoxy]-1-(1-naphthyl)ethanol hydrochloride

TABLE 1

| | | Administration Group of Compound A Maleate | Administration Group of Compound A oxide Maleate |
|---|---|---|---|
| Plasma | $T_{1/2}$ (Hours) | 1.56 | 2.69 |
| | MRT (Hours) | 2.86 | 5.41 |
| Brain | $T_{1/2}$ (Hours) | 1.53 | 2.28 |
| | MRT (Hours) | 3.01 | 5.72 |

The residence time of the compound A in the body was prolonged by the administration of the compound A oxide, and the concentration of the compound A in the plasma and brain was maintained at a high concentration.

INDUSTRIAL APPLICABILITY

A benzothiophene oxide derivative represented by the general formula [1] or a salt thereof is useful as a prodrug of a corresponding benzothiophene derivative or a salt thereof. Further, a benzothiophene oxide derivative represented by the general formula [1] or a salt thereof is useful as a drug substance of a long-acting preparation of a corresponding benzothiophene derivative or a salt thereof.

The invention claimed is:

1. A benzothiophene oxide derivative represented by the following general formula or a salt thereof:

[Formula 1]

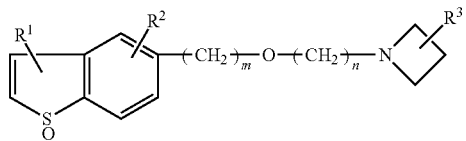

wherein, $R^1$ and $R^2$ are the same or different and represent one or more groups selected from a hydrogen atom, a halogen atom, an alkyl, aryl, aralkyl, alkoxy, aryloxy, alkylthio, arylthio, alkenyl, alkenyloxy, amino, alkylsulfonyl, arylsulfonyl, carbamoyl or heterocyclic group which may be substituted, an amino, hydroxyl or carboxyl group which may be protected, a nitro group and an oxo group; $R^3$ represents an alkylamino group which may be substituted, an amino or hydroxyl group which may be protected; and m and n are the same or different and each represent an integer of 1 to 6.

2. The benzothiophene oxide derivative or a salt thereof according to claim 1, wherein $R^1$ is a hydrogen atom; and $R^2$ is a hydrogen atom, a halogen atom or an alkoxy group.

3. The benzothiophene oxide derivative or a salt thereof according to claim 1 or 2, wherein m is 2; and n is 2 or 3.

4. The benzothiophene oxide derivative or a salt thereof according to claim 1, wherein $R^2$ is a hydrogen atom; $R^3$ is a hydroxyl group; and n is 3.

5. 1-(3-(2-(1-benzothiophen-5-yl)ethoxy)propyl)azetidin-3-ol S-oxide or a salt thereof.

6. A pharmaceutical composition containing the benzothiophene oxide derivative or a salt thereof according to claim 1.

7. The benzothiophene oxide derivative or a salt thereof according to claim 2, wherein $R^2$ is a hydrogen atom; $R^3$ is a hydroxyl group; and n is 3.

8. The benzothiophene oxide derivative or a salt thereof according to claim 3, wherein $R^2$ is a hydrogen atom; $R^3$ is a hydroxyl group; and n is 3.

9. A pharmaceutical composition containing the benzothiophene oxide derivative or a salt thereof according to claim 2.

10. A pharmaceutical composition containing the benzothiophene oxide derivative or a salt thereof according to claim 3.

11. A pharmaceutical composition containing the benzothiophene oxide derivative or a salt thereof according to claim 4.

12. A pharmaceutical composition containing the benzothiophene oxide derivative or a salt thereof according to claim 5.

* * * * *